United States Patent
Akagane

(10) Patent No.: US 10,357,273 B2
(45) Date of Patent: Jul. 23, 2019

(54) MEDICAL DEVICE AND COATING MATERIAL

(71) Applicant: OLYMPUS CORPORATION, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 288 days.

(21) Appl. No.: 15/261,145

(22) Filed: Sep. 9, 2016

(65) Prior Publication Data

US 2016/0374744 A1    Dec. 29, 2016

Related U.S. Application Data

(63) Continuation of application No. PCT/JP2016/064047, filed on May 11, 2016.

(30) Foreign Application Priority Data

Apr. 29, 2015 (JP) .................................. 2015-110243

(51) Int. Cl.
*A61B 18/12* (2006.01)
*A61B 17/32* (2006.01)
(Continued)

(52) U.S. Cl.
CPC ...... *A61B 17/320092* (2013.01); *A61B 18/14* (2013.01); *A61B 18/1445* (2013.01);
(Continued)

(58) Field of Classification Search
CPC ............ A61B 17/320092; A61B 18/14; A61B 18/1445; A61B 2018/00065;
(Continued)

(56) References Cited

U.S. PATENT DOCUMENTS 5,400,602 A * 3/1995 Chang .................... A61B 18/02
128/DIG. 27
5,562,659 A * 10/1996 Morris ................... A61B 18/14
600/396

(Continued)

FOREIGN PATENT DOCUMENTS

JP    2001-057982 A    3/2001
JP    2001-180647 A    7/2001
(Continued)

OTHER PUBLICATIONS

English translation of International Preliminary Report on Patentability dated Dec. 14, 2017 together with the Written Opinion received in related International Application No. PCT/JP2016/064047.

(Continued)

*Primary Examiner* — Daniel W Fowler
(74) *Attorney, Agent, or Firm* — Scully, Scott, Murphy & Presser, P.C.

(57) ABSTRACT

A coating material and a medical device. The medical device having an end effector and a coating to cover the end effector. The coating having one or more of: a plurality of hollow particles; and projections and depressions.

23 Claims, 10 Drawing Sheets

(51) Int. Cl.
*A61B 18/14* (2006.01)
*A61B 18/00* (2006.01)

(52) U.S. Cl.
CPC ............. *A61B 2018/00065* (2013.01); *A61B 2018/00101* (2013.01); *A61B 2018/00107* (2013.01); *A61B 2018/00125* (2013.01); *A61B 2018/00994* (2013.01)

(58) Field of Classification Search
CPC ........... A61B 2018/00101; A61B 2018/00107; A61B 2018/00125; A61B 2018/00994
See application file for complete search history.

(56) References Cited

U.S. PATENT DOCUMENTS

| | | | |
|---|---|---|---|
| 2002/0082556 A1* | 6/2002 | Cioanta | A61B 18/04 604/113 |
| 2003/0125732 A1* | 7/2003 | Goble | A61B 18/14 606/48 |
| 2005/0154385 A1* | 7/2005 | Heim | A61B 18/1402 606/41 |
| 2008/0064982 A1* | 3/2008 | Nowlin | A61B 10/06 600/564 |
| 2009/0143806 A1 | 6/2009 | Witt et al. | |
| 2011/0028964 A1* | 2/2011 | Edwards | A61B 18/1442 606/33 |
| 2012/0196129 A1 | 8/2012 | Okumura et al. | |
| 2014/0005668 A1* | 1/2014 | Rhee | A61B 17/320092 606/45 |
| 2014/0135804 A1* | 5/2014 | Weisenburgh, II | A61B 17/320092 606/169 |
| 2015/0148832 A1 | 5/2015 | Boudreaux et al. | |
| 2015/0297289 A1 | 10/2015 | Hirai et al. | |

FOREIGN PATENT DOCUMENTS

| | | |
|---|---|---|
| JP | 2001-355960 A | 12/2001 |
| JP | 2011-515198 A | 2/2011 |
| JP | 2015-011056 A | 1/2015 |
| WO | 2011/046122 A1 | 4/2011 |
| WO | 2012/116957 A1 | 9/2012 |
| WO | 2014/196641 A1 | 12/2014 |

OTHER PUBLICATIONS

Japanese Office Action dated Jan. 31, 2017 in Japanese Patent Application No. 2016-572348.
International Search Report dated Aug. 16, 2016 issued in International Application No. PCT/JP2016/064047.
Extended Supplementary European Search Report dated Nov. 19, 2018 in European Patent Application No. 16 80 3005.4.

* cited by examiner

MEDICAL DEVICE AND COATING MATERIAL

CROSS-REFERENCE TO RELATED APPLICATION

This application is a Continuation application of PCT International Application No. PCT/JP2016/064047, filed on May 11, 2016, and claims the benefit of priority from prior Japanese Patent Application No. 2015-110243, filed on May 29, 2015. The entire contents of PCT International Application No. PCT/JP2016/064047 and Japanese Patent Application No. 2015-110243 are incorporated herein by reference.

BACKGROUND

Technical Field

The present invention relates to a medical device for treating biological tissue using energy of ultrasonic vibration and the like, and to a coating material.

Background Art

Ultrasonic surgical blades are available as minimally invasive surgical instruments, as disclosed in Patent Document 1 (Japanese Translation of PCT International Application Publication No. 2011-505198). Such an ultrasonic surgical blade generates mechanical vibration at an ultrasonic frequency using an ultrasonic transducer, and transmits the mechanical vibration to an end effector through a transmission component. The vibrational motion of the end effector generates heat in tissue, to cut and coagulate the tissue.

SUMMARY

There has been demand for more minimally invasive medical devices, to reduce the burden on patients.

To achieve the object stated above, a medical device according to one aspect of the present invention comprises: an end effector configured to output energy to perform a treatment, wherein the end effector is heated in performing the treatment; and a first coating configured to cover the end effector, wherein the first coating defines a plurality of hollow spaces.

To achieve the object stated above, a medical device according to another aspect of the present invention comprises: an end effector configured to output energy to perform a treatment, wherein the end effector is heated in the process of performing the treatment; and a coating configured to cover the end effector, wherein the coating defines a plurality of projections and depressions.

To achieve the object stated above, a medical device according to another aspect of the present invention comprises: an end effector configured to output energy to perform a treatment, wherein the end effector is heated in the process of performing the treatment; and a coating configured to cover the end effector, wherein the coating defines a plurality of hollow spaces, projections and depressions.

To achieve the object stated above, a coating material according to another aspect of the present invention comprises: a resin as a base material; a plurality of hollow particles of a first type, wherein each of the plurality of hollow particles of the first type has a size with is within a first size distribution; and a plurality of hollow particles of a second type, wherein each of the plurality of hollow particles of the second type has a size within a second size distribution, different from the first size distribution, wherein the plurality of hollow particles of the first type and the plurality of hollow particles of the second type are mixed with the resin.

With the structures described above, a more minimally invasive medical device can be provided.

DETAILED DESCRIPTION

Embodiment 1

The following describes Embodiment 1 of a medical device according to the present invention, with reference to FIGS. 1 to 11.

Figure 1:
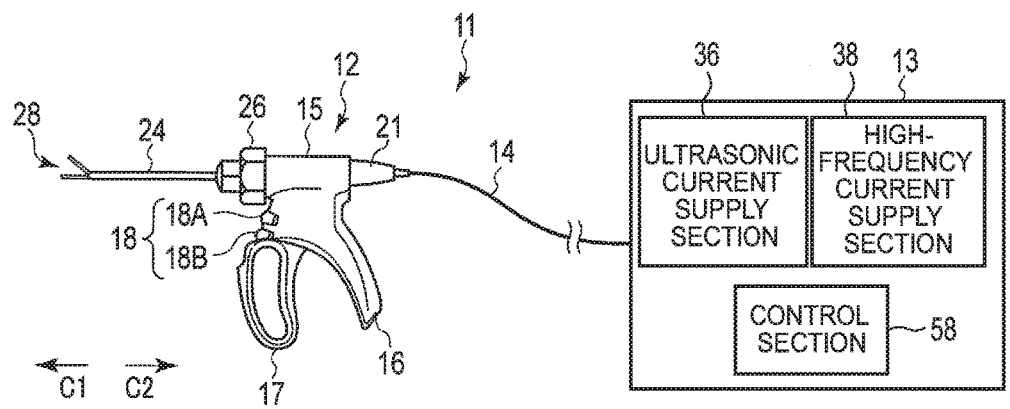
FIG. 1 is a schematic view illustrating the overall structure of a medical device in Embodiment 1.

As illustrated in FIG. 1, a medical device 11 includes a handpiece 12, a power unit 13, and a cable 14 connecting the handpiece 12 and the power unit 13.

As illustrated in FIGS. 1 to 4, the handpiece 12 includes: a housing 15 forming an outer envelope; a fixed handle 16 formed integrally with the housing 15; a handle 17 rotatable with respect to the housing 15; a plurality of operation buttons 18 provided on the housing 15; a vibration generation section 22 (transducer) housed in a case 21 removable from the housing 15; a rod-shaped vibration transmission member 23 (probe) connected to the vibration generation section 22; a cylindrical sheath 24 (tubular member) configured to cover the periphery of the vibration transmission member 23 to protect the vibration transmission member 23; a ring-shaped support section 25 (lining) placed between the vibration transmission member and the sheath 24; a knob 26 (rotating knob) fixed to the sheath 24; a jaw 27 rotatable with respect to the vibration transmission member 23 and the sheath 24; a cylindrical movable pipe placed inside the sheath 24 and moving forward and backward when the jaw 27 is opened and closed; an end effector 28 placed on the distal side of the vibration transmission member 23; and a coating 31 (coating material) configure to cover a part of the end effector 28. In this embodiment, one of the two directions parallel to the longitudinal direction C of the vibration transmission member 23 is referred to as the distal direction C1, and the direction opposite to the distal direction as the proximal direction C2.

Figure 3:
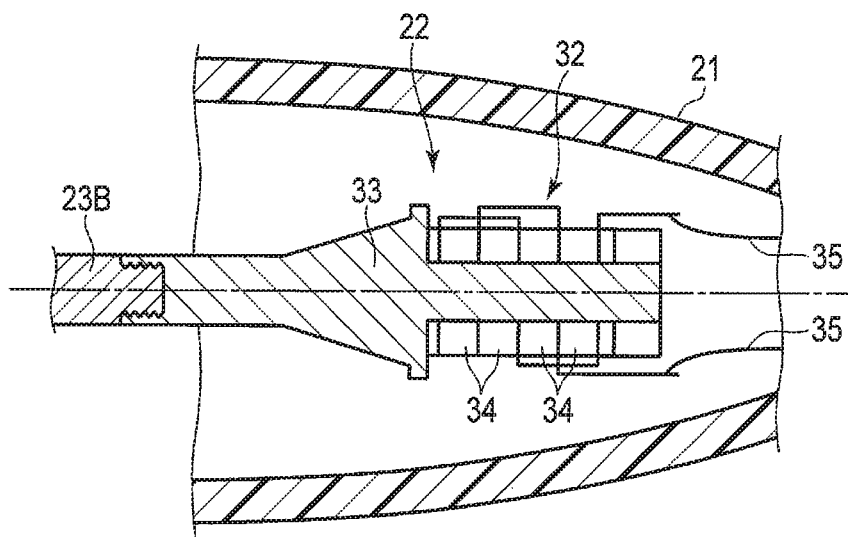
FIG. 3 is a sectional view illustrating a vibration generation section in the medical device illustrated in FIG. 1.

As illustrated in FIG. 3, the vibration generation section 22 includes an ultrasonic vibrator 32 and a horn member 33. The ultrasonic vibrator 32 is provided with a plurality of piezoelectric elements 34 (for example, four piezoelectric elements 34 in this embodiment) for changing current into ultrasonic vibration. The ultrasonic vibrator 32 is connected to one end of an electric wire 35. The electric wire 35 passes through the cable 14, and is connected to an ultrasonic current supply section 36 in the power unit 13 at the other end. When power is supplied from the ultrasonic current supply section 36 to the ultrasonic vibrator 32 through the electric wire 35, the ultrasonic vibrator 32 generates ultrasonic vibration.

As illustrated in FIG. 3, the ultrasonic vibrator 32 is attached to the horn member 33. The horn member 33 is made of a metal material. The horn member 33 has a substantially conical cross-section change part that decreases in cross section in the distal direction C1 of the vibration transmission member 23. The amplitude of the ultrasonic vibration generated by the ultrasonic vibrator 32 is expanded in the cross-section change part.

Figure 4:
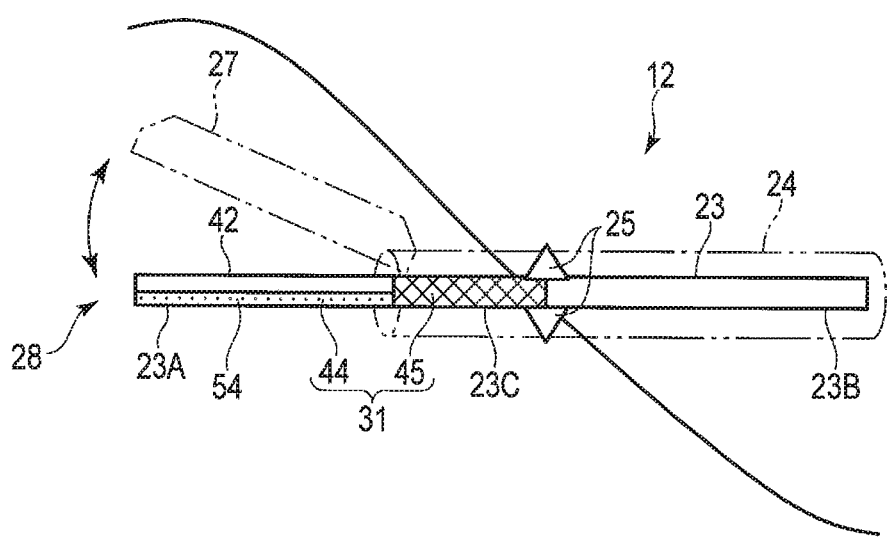
FIG. 4 is a side view illustrating a first part and second part of a coating provided on the vibration transmission member illustrated in FIG. 1.

As illustrated in FIG. 4, the support section 25 is placed at the node position of the ultrasonic vibration (indicated by the sine curve in the drawing) generated by the vibration generation section 22. The support section 25 supports the vibration transmission member 23, and also seals the inside of the sheath 24 so that no liquid or fragment of treated biological tissue enters through the support section 25 in the proximal direction C2.

Figure 2:
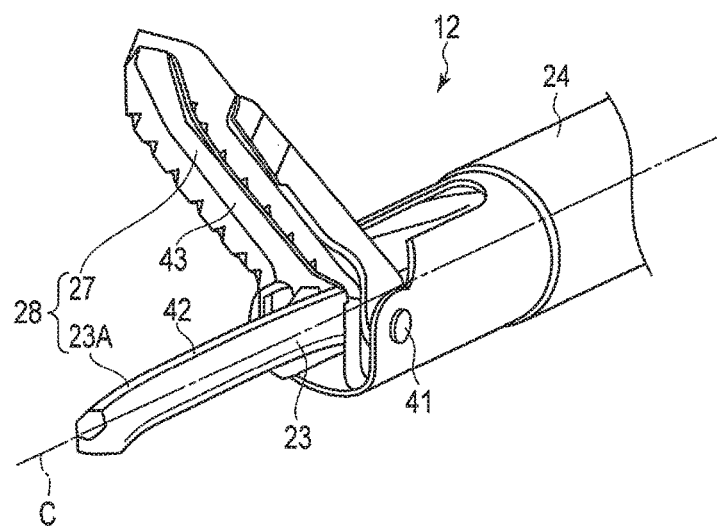
FIG. 2 is a perspective view illustrating a distal section and jaw of a vibration transmission member of a handpiece in the medical device illustrated in FIG. 1.
Figure 5A:
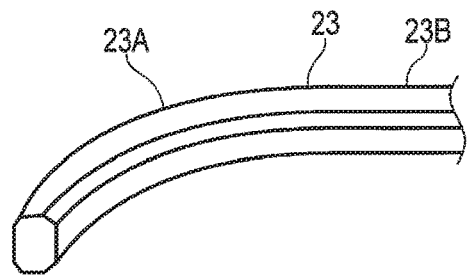
FIG. 5A is a top view illustrating the distal section of the vibration transmission member illustrated in FIG. 4.
Figure 5B:
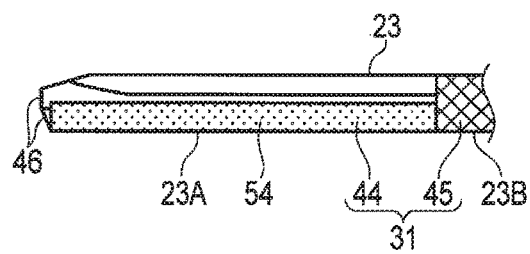
FIG. 5B is a side view illustrating the distal section of the vibration transmission member illustrated in FIG. 5A.

As illustrated in FIGS. 2, 4, and 5, the vibration transmission member 23 (probe) is, for example, made of a biocompatible metal material (such as a titanium alloy), in the shape of a rod curved laterally on the distal side. The vibration transmission member 23 includes: a distal section 23A on the distal direction C1 side; a proximal section 23B on the proximal direction side; and an intermediate section 23C between the distal section 23A and the proximal section 23B. The distal section 23A and the intermediate section 23C constitute a part of the end effector 28. The proximal section 23B is connected to one of two second electric wires. The second electric wire passes through the cable 14, and is electrically connected to one output terminal of a high-frequency current supply section 38 at the other end.

Thus, ultrasonic vibration is transmitted to the vibration transmission member 23 from the vibration generation section 22, and also high-frequency current is supplied to the vibration transmission member 23 from the high-frequency current supply section 38. This enables the vibration transmission member 23 to not only impart ultrasonic vibration to the biological tissue, but also function as one pole of a bipolar electrode for performing bipolar treatment.

As illustrated in FIGS. 1 and 2, the sheath 24 is cylindrical, and protects the vibration transmission member located inside. The sheath 24 is attached to the housing 15 rotatably with respect to the housing 15, at its proximal part. The knob 26 is fixed to the sheath 24. By rotating the knob 26 with respect to the housing 15, the sheath 24, the vibration transmission member 23, the ultrasonic vibrator 32, and the jaw 27 can be rotated integrally about the central axis C. The sheath 24 has a support pin 41 for supporting the jaw 27 in the distal section 23A. The proximal part of the sheath 24 is connected to the other one of the two second electric wires. The other second electric wire passes through the cable 14, and is electrically connected to the other output terminal of the high-frequency current supply section 38 at the other end.

The jaw 27 is an example of a clamp member rotatable about the support pin 41 between a contact position where the jaw 27 is in contact with the vibration transmission member 23 and a separate position where the jaw 27 is separate from the vibration transmission member 23, as indicated by the arrow in FIG. 4. The jaw 27 is electrically connected to the sheath 24 through the support pin 41. This enables the jaw 27 at the distal end of the sheath 24 to function as the other pole of the bipolar electrode for performing bipolar treatment. The electrode part of the jaw 27 is, for example, made of a copper alloy.

As illustrated in FIGS. 2 and 4, the end effector 28 is composed of the distal section 23A (first grasping piece) and intermediate section 23C of the vibration transmission member 23 and the jaw 27 (second grasping piece). The part of the distal section 23A of the vibration transmission member 23 facing the jaw 27 forms a first treatment surface 42. The part of the jaw 27 facing the vibration transmission member 23 forms a second treatment surface 43. In the treatment, the operator operates the end effector 28 like forceps by opening and closing the jaw 27, to sandwich and hold the treatment object between the distal section 23A and the jaw 27. In this holding state, the end effector 28 imparts, to the treatment object (biological tissue), treatment energy (ultrasonic energy, electric energy) for cauterizing, incising, or both cauterizing and incising the biological tissue, to perform the treatment such as excising and coagulating the biological tissue. Although this embodiment describes the treatment energy as ultrasonic energy and/or electric energy, any single energy or appropriate combination of ultrasonic energy, high-frequency energy, heat energy, light energy, an electromagnetic wave, and kinetic energy may be output.

The operator can open and close the jaw 27 by rotating the handle 17 with respect to the housing 15. In detail, when the operator operates the handle 17, the movable pipe inside the sheath 24 moves forward and backward along the central axis C of the sheath 24, thus opening and closing the jaw 27.

The coating 31 (coating material) has a first part 44 configured to cover the distal section 23A of the vibration transmission member 23, and a second part 45 configured to cover the intermediate section 23C of the vibration transmission member 23. For example, the coating has an appropriate thickness depending on use in the range of 10 μm to 200 μm. The coating 31 is made of an electrically insulating resin material.

As illustrated in FIG. 4, the first part 44 is provided on the part of the distal section 23A of the vibration transmission member 23 exposed to outside from the sheath 24. In more detail, the first part 44 covers the part of the distal section 23A of the vibration transmission member 23 on the side opposite to the first treatment surface 42 facing the jaw 27. The first part 44 is away from a distal component 46 (tapered section, inclined section, chamfered section) forming a probe distal surface at the most distal end of the distal section 23A, as illustrated in FIG. 5 in more detail.

Figure 6:
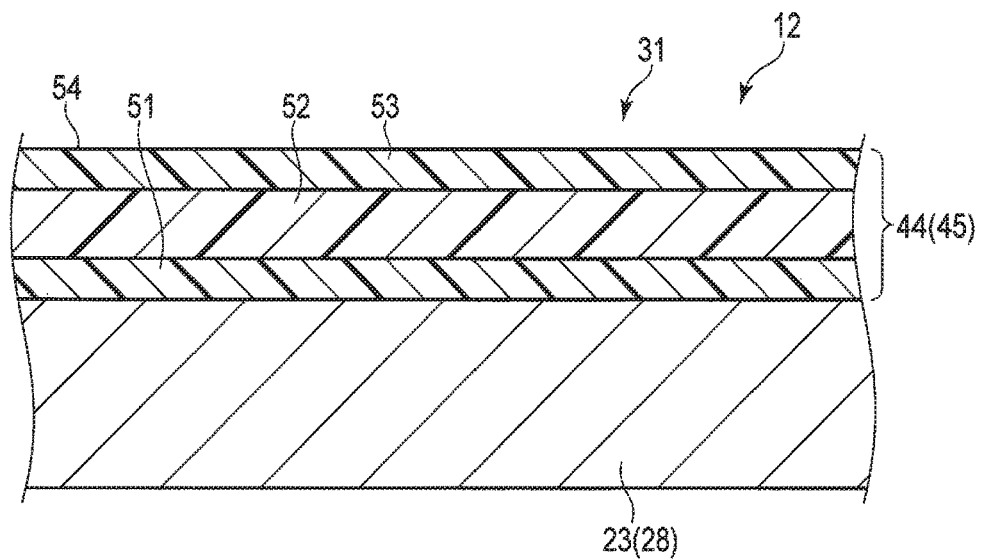
FIG. 6 is a sectional view schematically illustrating each layer of the coating (first part and second part) illustrated in FIG. 4.
Figure 7:
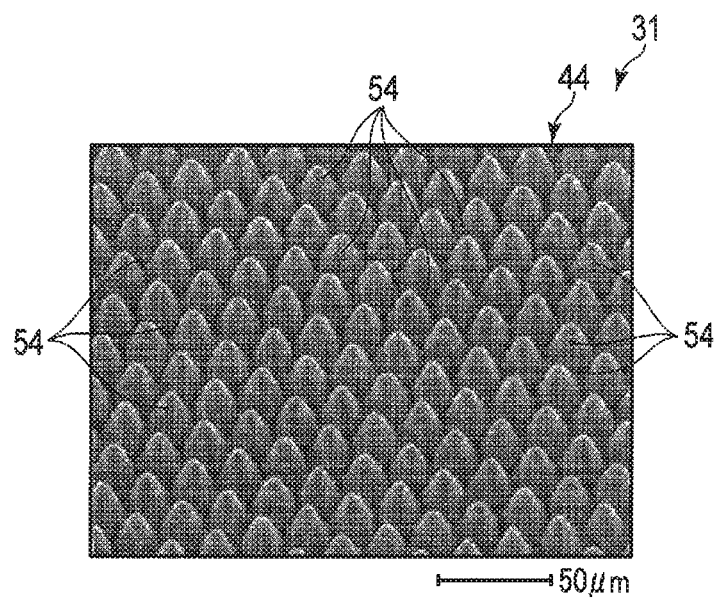
FIG. 7 is a perspective view illustrating the projections and depressions of the first part of the coating illustrated in FIG. 4.

As illustrated in FIG. 6, the first part 44 includes: a first layer 51 as a base layer; a second layer 52 on top of the first layer 51; and a third layer 53 on top of the second layer 52. The first layer 51 and the third layer 53 are each a typical coating made of a resin material such as PEEK (a resin not containing hollow particles, i.e. a second resin). The outermost third layer has projections and depressions 54 on its surface, as illustrated in FIG. 7. For example, the projections and depressions 54 of the third layer 53 can be formed transcriptionally by the following method. A metal round bar having a plurality of projections and depressions formed on its surface in a knurling manner is heated to several hundred degrees and, while rotating the heated round bar and the first part 44 (the vibration transmission member 23) with respect to each other, the round bar is pressed against the first part 44. As a result, the projections and depressions 54 are formed transcriptionally on the first part 44.

By transcriptionally forming the projections and depressions 54 in this way, the state of the surface can be made more uniform (projections and depressions are arranged with a uniform pitch as illustrated in FIG. 7) as compared with, for example, the case of enhancing surface roughness by sandblasting or the like. This contributes to stable performance of not conveying heat to surrounding tissue that unintentionally comes into contact with the part.

Figure 8:
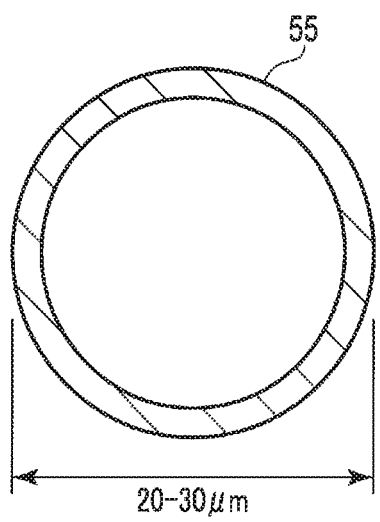
FIG. 8 is a sectional view schematically illustrating a first hollow particle contained in a second layer of the first part and second part of the coating illustrated in FIG. 4.

The second layer 52 is formed by dispersively mixing first hollow particles 55 and second hollow particles 56 with a base material made of PEEK resin. As illustrated in FIG. 8, each first hollow particle 55 (first hollow particle) is hollow spherical glass (soda lime borosilicate glass) or silica (silicon dioxide). The particle size of each first hollow particle 55 is distributed, for example, in the range of 20 μm to 30 μm.

Figure 9:
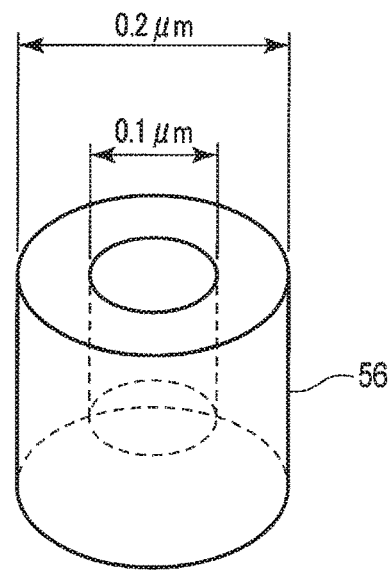
FIG. 9 is a sectional view schematically illustrating a second hollow particle contained in the second layer of the first part and second part of the coating illustrated in FIG. 4.

As illustrated in FIG. 9, each second hollow particle 56 (second hollow particle) is hollow and bottomed cylindrical glass (soda lime borosilicate glass) or silica (silicon dioxide). The particle size of each second hollow particle 56 is, for example, about 0.2 μm. Thus, the particle size distribution of the second hollow particles 56 is different from the particle size distribution of the first hollow particles 55. Each second hollow particle 56 has a hole of about 0.1 μm inside. Hence, a hollow space (a space filled with air) is formed inside each of the first hollow particles 55 and second hollow particles 56.

As illustrated in FIG. 4, the second part 45 is provided on the part of the intermediate section 23C of the vibration transmission member 23 covered with the sheath 24. The second part 45 covers the part of the intermediate section 23C of the vibration transmission member 23 on the distal direction C1 side of the support section 25 (the node position of ultrasonic vibration). The second part 45 includes: a first layer 51 having the same composition as and formed continuously with the first layer 51 of the first part 44; a second layer 52 having the same composition as and formed continuously with the second layer 52 of the first part 44; and a third layer 53 having the same composition as and formed continuously with the third layer 53 of the first part 44. The second layer 52 is overlaid on top of the first layer 51, and the third layer 53 is overlaid on top of the second layer 52. The first layer 51 and the third layer 53 are each a typical coating made of a resin material such as PEEK (a resin not containing hollow particles, i.e. a second resin). The third layer 53 of the second part 45 is flat.

As illustrated in FIG. 1, the power unit 13 includes: the ultrasonic current supply section 36 (ultrasonic energy supply section); the high-frequency current supply section 38 (high-frequency energy supply section); and a control section 58 that controls the ultrasonic current supply section 36 and the high-frequency current supply section 38. The control section 58 can control the supply of ultrasonic generation current from the ultrasonic current supply section 36 and the supply of high-frequency current from the high-frequency current supply section 38. When the operator operates any of the operation buttons 18, an electric signal is transmitted to the control section 58, and energy operation input is detected. The control section 58 accordingly supplies ultrasonic generation current from the ultrasonic current supply section 36 to the vibration generation section 22, and supplies high-frequency current from the high-frequency current supply section 38 to the end effector 28.

The plurality of operation buttons 18 include: a first operation button 18A corresponding to a coagulation mode; and a second operation button 18B corresponding to a coagulation and incision mode. For example, when the operator operates the first operation button 18A, the end effector 28 outputs ultrasonic energy and high-frequency energy suitable for biological tissue coagulation under control of the control section 58. When the operator operates the second operation button 18B, the end effector outputs ultrasonic energy and high-frequency energy suitable for biological tissue coagulation and incision under control of the control section 58.

Figure 10:
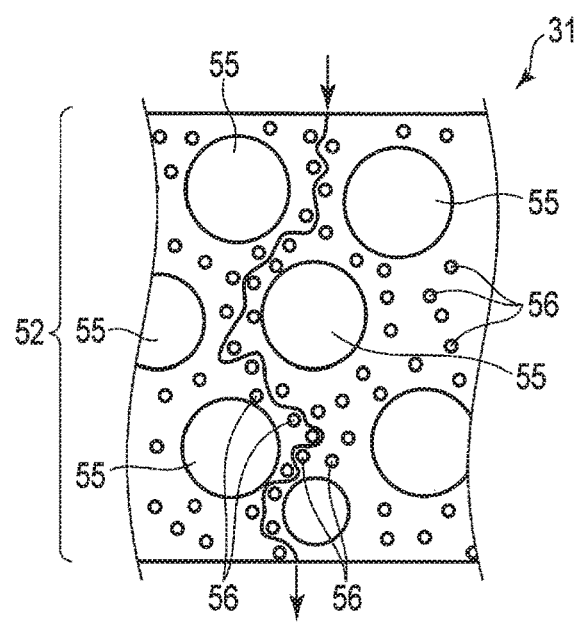
FIG. 10 is a sectional view schematically illustrating a heat conduction path in the second layer of the first part and second part of the coating illustrated in FIG. 4.

The functions of the medical device 11 in this embodiment are described below, with reference to FIGS. 1, 10, and 11.

In the treatment, the operator can sandwich the biological tissue between the vibration transmission member 23 and the jaw 27 by operating the handle 17. The operator can then feed energy into the sandwiched biological tissue by operating any of the operation buttons 18. When the operator operates the second operation button 18B corresponding to the coagulation and incision mode, the vibration transmission member 23 performs ultrasonic vibration, to impart heat energy (ultrasonic energy) by frictional motion to the biological tissue. At the same time, high-frequency current flows into the biological tissue between the vibration transmission member 23 and jaw constituting the bipolar electrode, to impart high-frequency energy to the biological tissue. The biological tissue can be coagulated and incised using these two types of energy.

Moreover, when the operator operates the first operation button 18A while the biological tissue is sandwiched between the vibration transmission member 23 and the jaw 27, high-frequency current flows into the biological tissue sandwiched by the end effector 28, to feed high-frequency energy into the biological tissue. The biological tissue can be only coagulated in this way.

If the coagulation and incision treatment or the coagulation treatment is performed on the biological tissue (treatment object) for a long time, the end effector 28 may reach a high temperature exceeding 200° C. as an example. In this embodiment, the first part 44 and second part 45 of the coating 31 are formed on the vibration transmission member 23. The second layer 52 in each of the first part 44 and second part 45 contains the first hollow particles 55 and second hollow particles 56 that differ in particle size distribution and each have a heat insulation property. Accordingly, a heat conduction path in the second layer 52 from the end effector 28 to the third layer 53 bypasses the first hollow particles 55 and the second hollow particles 56, as illustrated in FIG. 10. This extends the heat conduction path severalfold as compared with the actual thickness of the second layer 52. The heat flux (the amount of heat conducted) in the cut-through direction of the coating 31 can thus be reduced.

The results of an experiment of evaluating the heat insulation property of the coating using pig liver are described below, with reference to FIG. 11. When pig liver comes into contact with high-temperature metal or the like, a phenomenon called heat denaturation, i.e. the burned part turning white, occurs. The experiment evaluated the heat insulation property using such heat denaturation of pig liver. In the experiment, the heat insulation property of the coating 31 was evaluated using, as the end effector 28, a metal plate (titanium alloy) having various coatings (heat insulation coatings). In the experiment, first to fifth areas 61 to 65 were set in the metal plate by setting various conditions. In the second to fifth areas 62 to 65, the coating 31 was formed on the surface of the metal plate. In the first area 61, the metal plate was exposed without forming the coating 31 (heat insulation coating). The coating 31 (heat insulation coating) in the second area 62 was made of a typical resin such as PEEK, and contained no hollow particles (heat insulation particles).

The coating 31 in the third area 63 was formed by mixing a particle mixture obtained by mixing the first hollow particles 55 (large) and the second hollow particles (small) at a ratio of 4:1, with a base material made of a typical resin such as PEEK at a predetermined ratio. The coating 31 in the fourth area 64 was formed by mixing a particle mixture obtained by mixing the first hollow particles 55 (large) and the second hollow particles 56 (small) at a ratio of 2:1, with a base material made of a typical resin such as PEEK at a predetermined ratio. The coating 31 in the fifth area 65 was formed by mixing a particle mixture obtained by mixing the first hollow particles 55 (large) and the second hollow particles 56 (small) at a ratio of 2:1, with a base material made of a typical resin such as PEEK at a predetermined ratio. The blending quantity of the particle mixture with the resin of the base material of the coating 31 in the fifth area 65 was twice that of the coating 31 in the third area 63. Meanwhile, the ratio of the first hollow particles 55 (large) and the second hollow particles 56 (small) in the coating 31 in the fifth area 65 was 4:1, i.e. the same as that in the third area 63.

In the experiment, the metal plate having the first to fifth areas 61 to 65 mentioned above was left in an oven at 125° C. for 30 minutes. After this, the metal plate was pressed against pig liver 66 for several seconds, and then separated from the pig liver 66.

Figure 11:
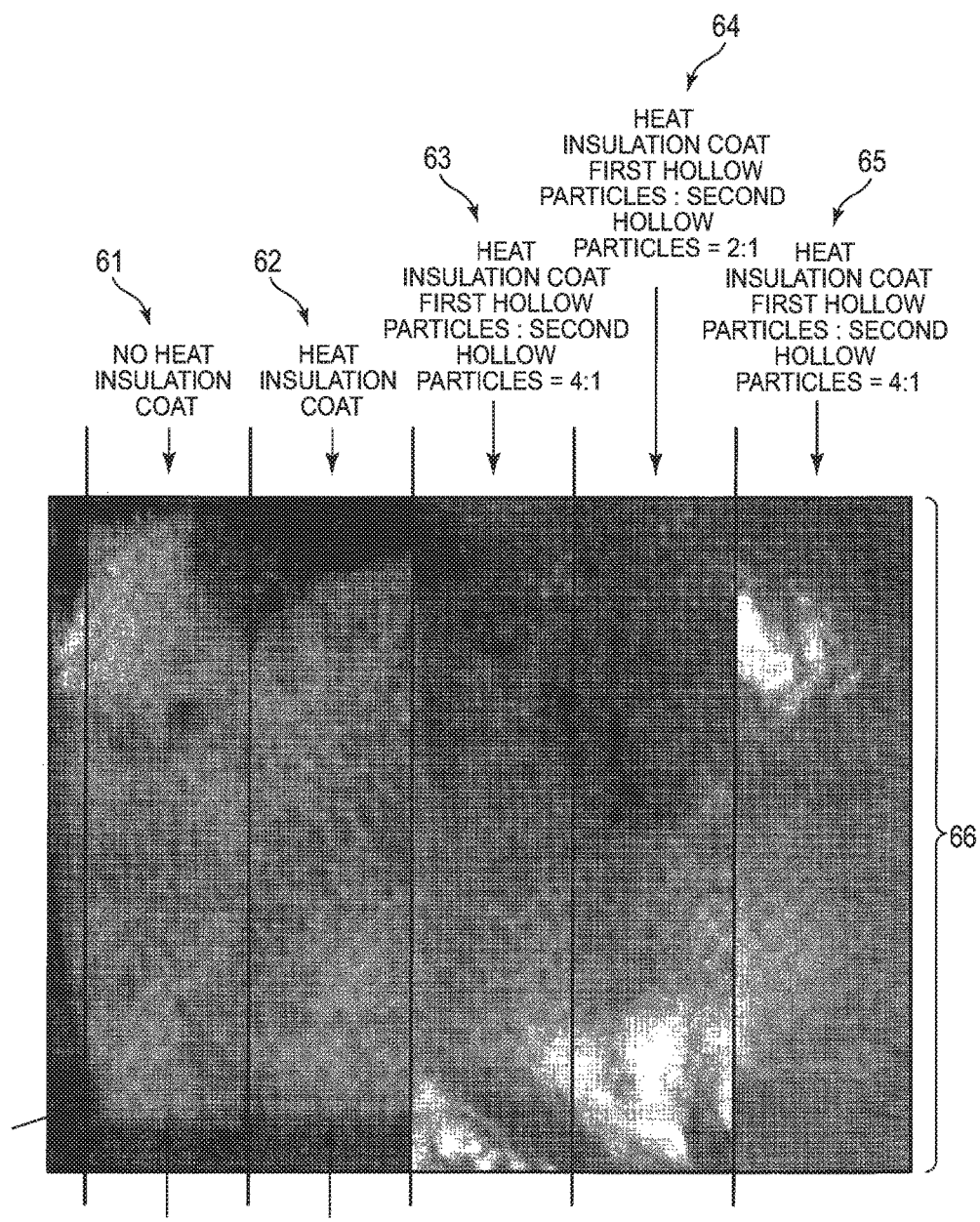
FIG. 11 is a photograph illustrating heat insulation test results (whether or not pig liver had heat denaturation) corresponding to first to fifth areas of a metal plate representing an end effector in the embodiment.

As illustrated in FIG. 11, the pig liver tissue brought into contact with the first area 61 and the pig liver tissue brought into contact with the second area 62 were found to have heat denaturation. The occurrence of heat denaturation can also be recognized from a clear boundary with the surrounding tissue not affected by heat, as indicated by the arrow in the drawing.

On the other hand, the pig liver tissue brought into contact with each of the third to fifth areas 63 to 65 was found to have no particular heat denaturation. The absence of heat denaturation can also be recognized from an unclear boundary with the surrounding tissue not affected by heat.

According to Embodiment 1, the medical device 11 includes: the end effector 28 to which vibration is transmitted; and the coating 31 configured to cover the end effector 28, and having at least either of: a hollow space; and the projections and depressions 54.

In the case where the coating 31 has a hollow space, the heat insulation effect of the hollow space makes it harder for the heat of the end effector 28 to be conducted to the surface of the coating 31. In the case where the coating 31 has the projections and depressions 54, the contact area with the surrounding tissue is reduced, to lower the heat conduction efficiency. Thus, even when the end effector 28 is erroneously brought into contact with surrounding tissue other than the treatment object, heat invasion to the surrounding tissue can be reduced.

With the structure described above, even in the case where the end effector 28 reaches a high temperature during the treatment, heat invasion to surrounding tissue other than the treatment object can be prevented by any of the hollow space and projections and depressions 54 of the coating 31.

The coating 31 has lower heat conductivity than the end effector 28. With such a structure, even in the case where the end effector 28 is unintentionally brought into contact with the surrounding tissue, the coating 31 with low heat conductivity suppresses heat invasion to the surrounding tissue. This reduces the burden on the patient and improves the workability of the operator.

The hollow space and the projections and depressions 54 inhibit heat conduction from the end effector 28 to the surface of the coating 31. With such a structure, the surface of the coating 31 can be kept from reaching a high temperature, thus preventing heat invasion to the surrounding tissue and reducing the burden on the patient.

The projections and depressions 54 are formed in a position exposed to outside. With such a structure, the projections and depressions 54 are formed on the surface of the vibration transmission member 23 which vibrates, in a position exposed to outside. This creates fine cavitation in the position where the projections and depressions 54 are formed. Hence, any fragment of biological tissue generated due to the treatment can be kept from adhering to the coating 31.

The coating 31 contains hollow particles. With such a structure, the coating 31 having the hollow space can be formed easily.

The coating 31 contains hollow particles of a plurality of types that differ in particle size distribution. Moreover, the coating material (the coating 31) includes: a resin as a base material; and hollow particles of a plurality of types that differ in particle size distribution and are mixed with the resin.

With such structures, the heat conduction path is formed so as to bypass the hollow particles. Such a heat conduction path is longer than the thickness of the coating 31, in the cut-through direction of the coating 31. In detail, the heat flux ($W/m^2$) which is the amount of heat conducted per unit area is proportional to the difference in temperature between both surfaces of a flat plate and also inversely proportional to the thickness of the flat plate, according to Fourier's law. In this embodiment, the heat flux of the coating 31 is as low as the heat flux of a thick coating. As a result, heat invasion to the surrounding tissue by the end effector 28 can be reduced. In addition, poor accessibility to a narrow gap of biological tissue, caused by extremely increasing the thickness of the coating 31, can be avoided.

The coating 31 contains the first hollow particles 55 and the second hollow particles 56 having a hollow shape different from that of the first hollow particles 55. With such a structure, the coating 31 in which the base material, the first hollow particles 55, and the second hollow particles 56 are mixed has a more complex composition, thus creating a longer heat conduction path in the thickness direction of the coating 31. The heat flux of such a coating 31 is as low as the heat flux of a thick coating, so that heat invasion to the surrounding tissue can be reduced.

The coating 31 includes: the first layer 51 attached tightly to the end effector 28, and made of a resin not containing the hollow particles; the second layer overlaid on top of the first layer 51, and made of a resin containing the hollow particles; and the third layer 53 overlaid on top of the second layer 52, and made of a resin not containing the hollow particles.

Typically, if the first hollow particles 55 and the second hollow particles 56 are mixed with the resin as the base material at a predetermined ratio as in the second layer 52 of the coating 31, the adhesion strength (bond strength) to the substrate (the vibration transmission member 23) or the film strength of the second layer 52 itself may decrease. According to this embodiment, since the second layer 52 in which such hollow particles are mixed is not in direct contact with the substrate, the adhesion strength can be maintained to reduce the risk of peeling of the coating 31. Moreover, since the second layer 52 is not the outermost layer, the film strength can be maintained to reduce the risk of cracking or peeling of the coating 31. Further, the coating 31 is made of resin, which ensures the electrical insulation property of the coating 31 and prevents the high-frequency current output from the end effector 28 from leaking and flowing to the surrounding cells.

The end effector 28 includes: the vibration transmission member 23 to which vibration is transmitted, and that is provided with the coating 31; and the clamp member movable between a contact position where the clamp member is in contact with the vibration transmission member and a separate position where the clamp member is separate from the vibration transmission member 23, and the coating 31 is provided on the side of the vibration transmission member 23 opposite to the side that comes into contact with the clamp member. With such a structure, the coating 31 is not located on the side where the clamp member for performing the treatment comes into contact, and so lower treatment efficiency caused by the coating 31 is prevented. Since the coating 31 is located in the part not involved in the treatment, the surrounding tissue is prevented from being damaged by heat even in the case where the part not involved in the treatment is erroneously brought into contact with the surrounding tissue.

The vibration transmission member 23 has the distal component 46 that forms a probe distal surface, and the coating 31 covers a part away from the distal component 46. When high-speed vibration such as ultrasonic vibration is made on the distal side of the vibration transmission member 23, cavitation occurs. Therefore, if the coating 31 is formed up to the distal end of the vibration transmission member 23, there is a possibility that the coating 31 is damaged or falls off due to cavitation. With the structure described above, the durability of the coating 31 can be improved by appropriately positioning the coating 31.

The medical device 11 includes the tubular member, and the end effector 28 includes the vibration transmission member 23: that is partly housed inside the tubular member; to which vibration is transmitted; and that is provided with the coating 31 in a part exposed from the tubular member. With such a structure, the coating 31 is formed on the exposed part that has a possibility of causing heat invasion to the surrounding tissue. This suppresses heat damage to the surrounding tissue.

Although the first hollow particles 55 and second hollow particles 56 that differ in particle size distribution are dispersively mixed in the second layer 52 of the coating 31 in this embodiment, for example, porous materials (e.g. pumice) of a plurality of types that differ in particle size distribution may be dispersively mixed in the second layer 52 of the coating 31 instead of the first hollow particles 55 and the second hollow particles 56.

Although hollow particles of two types that differ in particle size distribution are dispersively mixed in the second layer 52 of the coating 31 in this embodiment, hollow particles of three or more types that differ in particle size distribution may be dispersively mixed in the second layer 52 of the coating 31.

Although the first part 44 of the coating 31 is located on the side of the distal section of the vibration transmission member 23 opposite to the first treatment surface 42 facing the jaw 27 in this embodiment, the first part 44 of the coating 31 may be located to cover a part of the first treatment surface 42 in order to reduce the area of the first treatment surface 42.

Embodiment 2

Figure 12:
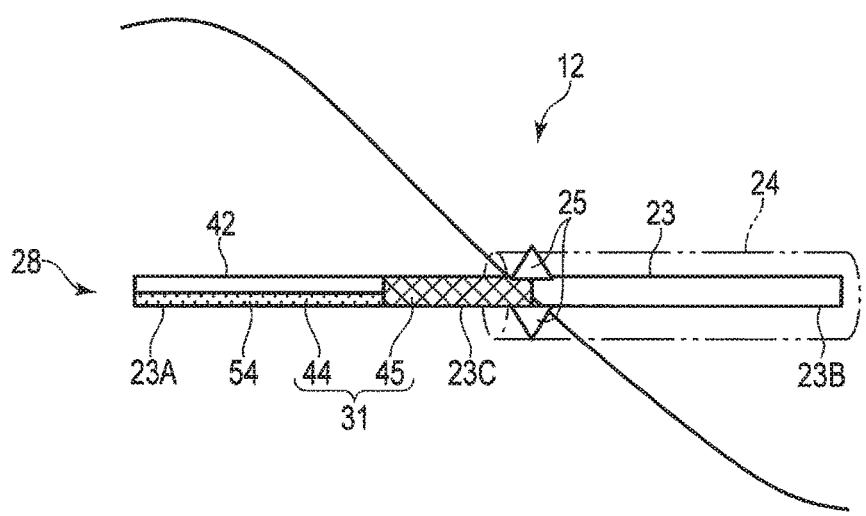
FIG. 12 is a schematic view illustrating the surroundings of a vibration transmission member of a handpiece in a medical device in Embodiment 2.

The following describes a medical device in Embodiment 2, with reference to FIG. 12. The medical device 11 in Embodiment 2 differs from that in Embodiment 1 in the shape of the end effector 28 and the end effector 28 forming a monopolar high-frequency treatment tool, but is the same as that in Embodiment 1 in the other parts. The following mainly describes the differences from Embodiment 1, and the illustration or description of the same parts as in Embodiment 1 is omitted.

In this embodiment, the handpiece 12 of the medical device 11 does not include the jaw 27. The end effector 28 is accordingly composed of only the vibration transmission member 23. The end effector 28 in this embodiment can be used as an active electrode in monopolar treatment, and enables flow of high-frequency current to a return electrode outside the patient's body. By feeding high-frequency energy into the biological tissue in this way, incision or excision treatment or coagulation treatment can be performed by the end effector 28. In this embodiment, ultrasonic energy can be fed into the biological tissue simultaneously with the above-mentioned high-frequency energy, as in Embodiment 1.

The medical device 11 has the same structure as the medical device in Embodiment 1 except those described above, and has the same functions and advantageous effects as the medical device in Embodiment 1.

Embodiment 3

Figure 13:
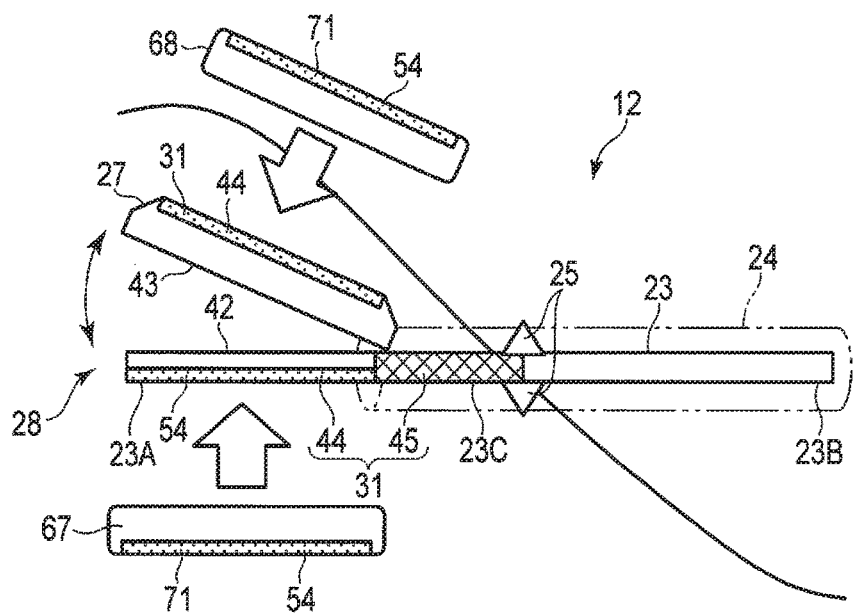
FIG. 13 is a schematic view illustrating the surroundings of a vibration transmission member of a handpiece in a medical device in Embodiment 3.

The following describes a medical device in Embodiment 3, with reference to FIG. 13. The medical device in Embodiment 3 differs from that in Embodiment 1 in that the coating 31 (the first part 44) is also formed on the jaw 27 and a first cover 67 and second cover 68 for protecting the surrounding tissue are included, but is the same as that in Embodiment 1 in the other parts. The following mainly describes the differences from Embodiment 1, and the illustration or description of the same parts as in Embodiment 1 is omitted.

In this embodiment, the first part 44 of the coating 31 same as that in Embodiment 1 is provided on the back surface of the jaw 27 opposite to the second treatment surface 43.

In this embodiment, the handpiece 12 of the medical device 11 further includes the first cover 67 configured to at least partially surround the end effector 28 in a radial direction of a longitudinal axis of the end effector 28 and the second cover 68 configured to at least partially surround the end effector 28 in a radial direction of a longitudinal axis of the jaw 27. The first cover 67 is configured to cover the side of the vibration transmission member 23 opposite to the first treatment surface 42. The second cover 68 is configured to cover the side of the jaw 27 opposite to the second treatment surface 43.

The first cover 67 is, for example, made of a biocompatible and insulating resin material (e.g. PEEK resin), and is removable from the distal part of the sheath 24. The first cover 67 has a second coating 71 on the side opposite to the side facing the end effector 28. The second coating 71 has the same structure as the first part 44 of the coating 31 in Embodiment 1.

The second cover 68 is, for example, made of a biocompatible and insulating resin material (e.g. PEEK resin), and is removable from the jaw 27 (clamp member). The second cover 68 has a second coating 71 on the side opposite to the side facing the end effector 28. The second coating 71 has the same structure as the first part 44 of the coating 31 in Embodiment 1.

The medical device 11 in this embodiment has substantially the same functions as that in Embodiment 1. Further, the handpiece 12 of the medical device 11 in this embodiment has the first part 44 of the coating 31 on the jaw 27. The handpiece 12 includes the first cover 67 having the second coating 71, and the second cover 68 equally having the second coating 71. Accordingly, even in the case where the end effector 28 is unintentionally brought into contact with the surrounding tissue during the treatment, the coating 31 of the jaw 27 and the second coating 71 of each of the first cover 67 and second cover 68 prevent heat invasion to the surrounding tissue.

According to Embodiment 3, the clamp member has the coating 31 having lower heat conductivity than the end effector 28, on the side opposite to the side facing the vibration transmission member 23.

The medical device 11 includes the cover 67, 68 configured to cover the end effector 28, and the cover 67, 68 has the second coating 71 having lower heat conductivity than the end effector 28, on the side opposite to the side facing the end effector 28.

With such structures, the risk of the operator unintentionally bringing the end effector 28 into contact with the surrounding tissue can be reduced by the first cover 67 and the second cover 68, thus reducing heat invasion to the surrounding tissue. Moreover, since the first cover 67 and the second cover 68 each have the second coating 71, the first cover 67 and the second cover 68 are kept from reaching a high temperature. Therefore, the surrounding tissue is prevented from being damaged by heat even in the case where the first cover 67 or the second cover 68 is brought into contact with the surrounding tissue during the treatment.

Although the first part 44 of the coating 31 is located on the back surface of the jaw 27 opposite to the second treatment surface 43 in this embodiment, the first part 44 of the coating 31 may be located to cover a part of the second treatment surface 43 of the jaw 27 in order to reduce the area of the second treatment surface 43. In this case, for example, a pair of first parts 44 of the coating 31 may be formed along the outer edges of the second treatment surface 43. Preferably, the pair of first parts 44 of the coating 31 each extend like a strip in the longitudinal direction of the jaw 27, and partly occupy the area of the part of the jaw 27 facing the vibration transmission member 23.

Embodiment 4

Figure 14:
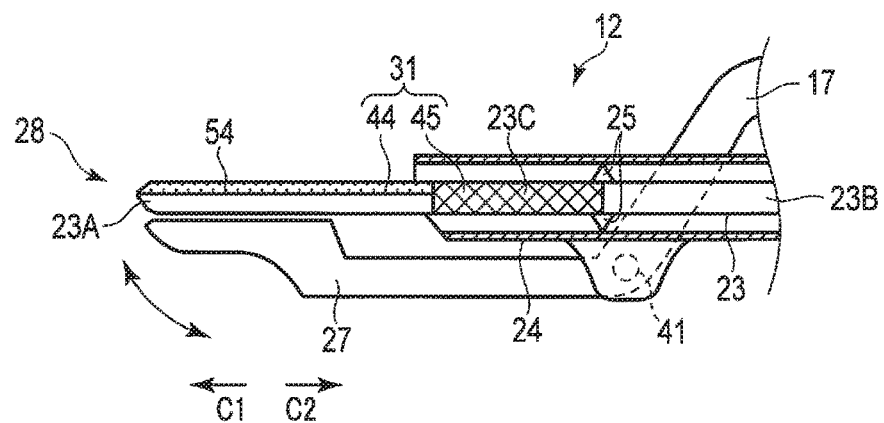
FIG. 14 is a sectional view illustrating a vibration transmission member, coating, jaw, and sheath of a handpiece in a medical device in Embodiment 4.

The following describes a medical device in Embodiment 4, with reference to FIG. 14. The medical device 11 in Embodiment 4 differs from that in Embodiment 1 in the attachment position and shape of the jaw 27, but is the same as that in Embodiment 1 in the other parts. The following mainly describes the differences from Embodiment 1, and the illustration or description of the same parts as in Embodiment 1 is omitted.

As illustrated in FIG. 14, the sheath 24 is cylindrical, and protects the vibration transmission member located inside. The sheath 24 has the support pin 41 for supporting the jaw 27 outside the cylinder near the distal section 23A. The other structure of the sheath 24 is the same as that in Embodiment 1.

In this embodiment, the jaw 27 (clamp member) is formed integrally with the handle 17 on the proximal direction C2 side. The jaw 27 is rotatable about the support pin 41 between a contact position where the jaw 27 is in contact with the vibration transmission member 23 and a separate position where the jaw 27 is separate from the vibration transmission member 23, as indicated by the arrow in FIG. 14. Here, the angle of rotation of the jaw 27 is larger and the length from the support pin 41 to the distal end of the jaw 27 is longer than in Embodiment 1. Therefore, for example, a larger treatment object (biological tissue) than in Embodiment 1 can be sandwiched and held.

The jaw 27 is electrically connected to the sheath 24 through the support pin 41. This enables the jaw 27 at the distal end of the sheath 24 to function as the other pole of the bipolar electrode for performing bipolar treatment. The electrode part of the jaw 27 is, for example, made of a copper alloy.

The functions and advantageous effects of this embodiment are substantially the same as those of Embodiment 1. This embodiment is particularly suitable for sandwiching and treating relatively large biological tissue, as the angle of rotation of the jaw 27 is larger and the length from the support pin 41 to the distal end of the jaw 27 is longer.

Embodiment 5

Figure 15:
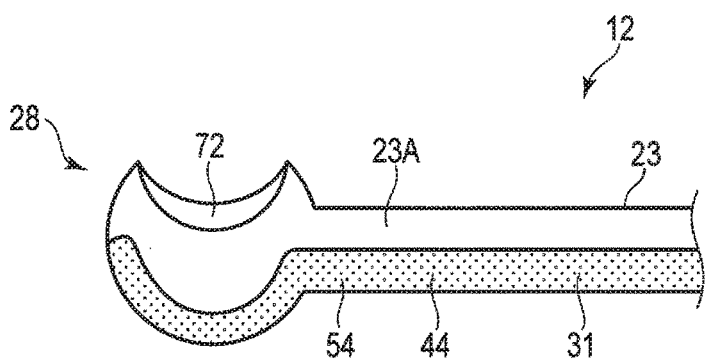
FIG. 15 is a sectional view illustrating a vibration transmission member and coating of a handpiece in a medical device in Embodiment 5.

The following describes a medical device in Embodiment 5, with reference to FIG. 15. The medical device 11 in Embodiment 5 differs from that in Embodiment 2 in the shape of the vibration transmission member 23, but is the same as that in Embodiment 2 in the other parts. The following mainly describes the differences from Embodiment 2, and the illustration or description of the same parts as in Embodiment 2 is omitted.

As illustrated in FIG. 5, the vibration transmission member 23 (probe) is, for example, made of a biocompatible metal material (such as a titanium alloy), in the shape of a rod. The vibration transmission member 23 includes: the distal section 23A on the distal side; the proximal section 23B on the opposite side to the distal section 23A; and the intermediate section 23C between the distal section 23A and the proximal section 23B. The distal section 23A and the intermediate section 23C constitute the end effector 28. The distal section 23A has a crescent cutter 72 (cutter face), and can incise, excise, etc. the biological tissue by the cutter 72.

The proximal section 23B is connected to one of the two second electric wires 37. Thus, ultrasonic vibration is transmitted to the vibration transmission member 23 from the vibration generation section 22, and also high-frequency current is supplied to the vibration transmission member 23 from the high-frequency current supply section 38. The vibration transmission member 23 (the end effector 28) in this embodiment can be used as an active electrode in monopolar treatment, and enables flow of high-frequency current to a return electrode outside the patient's body.

The coating 31 has the first part 44 configured to cover the distal section of the vibration transmission member 23, and the second part 45 configured to cover the intermediate section 23C of the vibration transmission member 23. For example, the coating 31 has an appropriate thickness depending on use in the range of 10 μm to 200 μm.

The first part 44 is provided on the part of the distal section of the vibration transmission member 23 exposed from the sheath 24. In more detail, the first part 44 covers the part of the distal section of the vibration transmission member 23 on the side opposite to the surface having the cutter 72. The other structure of the first part 44 and the structure of the second part 45 are the same as those in Embodiment 2.

The functions and advantageous effects of this embodiment are substantially the same as those of Embodiment 2. The end effector 28 having the cutter 72 in this embodiment is particularly suitable for incising or excising thick tissue or peeling thin-film tissue.

According to this embodiment, the end effector 28 includes the cutter face for incising the biological tissue, and the coating 31 is provided on the side opposite to the side where the cutter face is located. With such a structure, the coating 31 is not involved in the treatment by the cutter face, and so lower efficiency of the treatment by the cutter can be prevented.

First Modification of Embodiment 5

Figure 16:
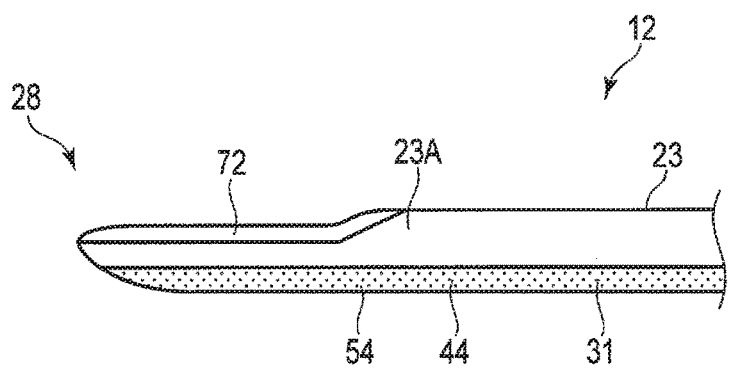
FIG. 16 is a side view illustrating a vibration transmission member and a coating in a first modification of Embodiment 5.

The following describes a medical device in a first modification of Embodiment 5, with reference to FIG. 16. The medical device 11 in the first modification differs from that in Embodiment 5 in the shape of the cutter 72 of the vibration transmission member 23, but is the same as that in Embodiment 5 in the other parts. The following mainly describes the differences from Embodiment 5, and the illustration or description of the same parts as in Embodiment 5 is omitted.

As illustrated in FIG. 16, the vibration transmission member 23 (probe) is, for example, made of a biocompatible metal material (such as a titanium alloy), in the shape of a rod. The vibration transmission member 23 includes: the distal section 23A on the distal side; the proximal section 23B on the side opposite to the distal section 23A; and the intermediate section 23C between the distal section 23A and the proximal section 23B. The distal section 23A and the intermediate section 23C constitute the end effector 28. The distal section 23A has a straight cutter 72, and can incise, etc. the biological tissue by the cutter 72. The other structure of the vibration transmission member 23 is the same as that in Embodiment 5.

The coating 31 has the first part 44 configured to cover the distal section 23A of the vibration transmission member 23, and the second part 45 configured to cover the intermediate section 23C of the vibration transmission member 23. For example, the coating 31 has an appropriate thickness depending on use in the range of 10 μm to 200 μm.

The first part 44 is provided on the part of the distal section of the vibration transmission member 23 exposed from the sheath 24. In more detail, the first part covers the part of the distal section 23A of the vibration transmission member 23 on the side opposite to the side having the cutter 72. The other structure of the first part 44 and the structure of the second part 45 are the same as those in Embodiment 5.

The functions and advantageous effects of the first modification are substantially the same as those of Embodiment 5. The end effector 28 having the cutter 72 in this embodiment is particularly suitable for incising or excising thick tissue.

Second Modification of Embodiment 5

Figure 17:
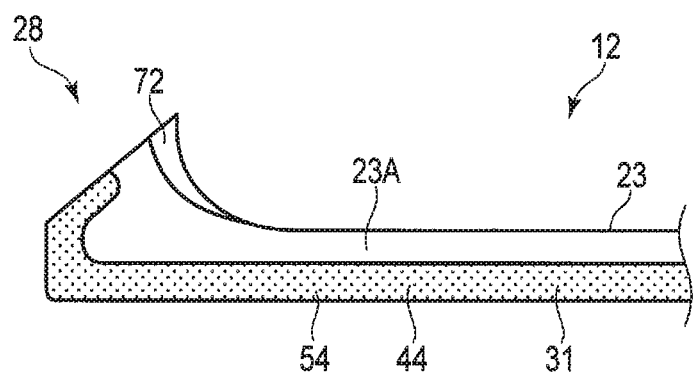
FIG. 17 is a side view illustrating a vibration transmission member and a coating in a second modification of Embodiment 5.

The following describes a medical device in a second modification of Embodiment 5, with reference to FIG. 17. The medical device 11 in the second modification differs from that in Embodiment 5 in the shape of the cutter 72 of the vibration transmission member 23, but is the same as that in Embodiment 5 in the other parts. The following mainly describes the differences from Embodiment 5, and the illustration or description of the same parts as in Embodiment 5 is omitted.

As illustrated in FIG. 1, the vibration transmission member 23 (probe) is, for example, made of a biocompatible metal material (such as a titanium alloy), in the shape of a rod. The vibration transmission member 23 includes: the distal section 23A on the distal side; the proximal section 23B on the side opposite to the distal section 23A; and the intermediate section 23C between the distal section 23A and the proximal section 23B. The distal section 23A and the intermediate section 23C constitute the end effector 28. The distal section 23A has a cutter 72 that rises from the shaft part like a rake, and can incise, etc. the biological tissue by the cutter 72. The other structure of the vibration transmission member 23 is the same as that in Embodiment 5.

The coating 31 has the first part 44 configured to cover the distal section 23A of the vibration transmission member 23, and the second part 45 configured to cover the intermediate section 23C of the vibration transmission member 23. For example, the coating 31 has an appropriate thickness depending on use in the range of 10 μm to 200 μm.

The first part 44 is provided on the part of the distal section of the vibration transmission member 23 exposed from the sheath 24. In more detail, the first part 44 covers the part of the distal section of the vibration transmission member 23 on the side opposite to the surface having the cutter 72. The other structure of the first part 44 and the structure of the second part 45 are the same as those in Embodiment 5.

The functions and advantageous effects of this embodiment are substantially the same as those of Embodiment 5. The cutter 72 in this embodiment is particularly suitable for perforating flat tissue, excising protruding biological tissue from its root, etc.

Embodiment 6

Figure 18:
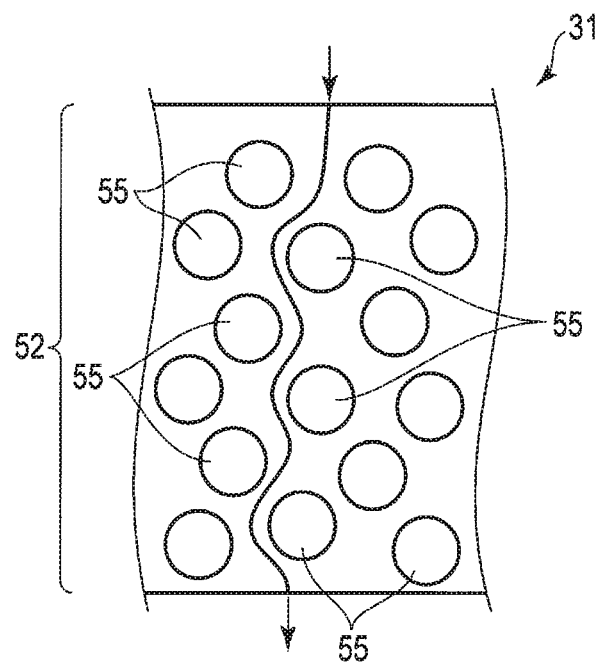
FIG. 18 is a sectional view schematically illustrating a heat conduction path in a second layer of a first part and second part of a coating in a medical device in Embodiment 6.

The following describes a medical device in Embodiment 6, with reference to FIG. 18. The medical device 11 in Embodiment 6 differs from that in Embodiment 1 in the composition of the second layer 52 of the first part and the second layer 52 of the second part 45 of the coating 31, but is the same as that in Embodiment 1 in the other parts. The following mainly describes the differences from Embodiment 1, and the illustration or description of the same parts as in Embodiment 1 is omitted.

The second layer 52 of the coating 31 (the first part 44, the second part 45) is formed by dispersively mixing first hollow particles 55 with a base material made of PEEK resin. Second hollow particles 56 are not mixed in this embodiment. Each first hollow particle 55 is hollow spherical glass (soda lime borosilicate glass) or silica (silicon dioxide). For example, the particle size of each first hollow particle 55 is 20 μm to 30 μm.

The functions of the medical device 11 in this embodiment are described below, with reference to FIG. 18.

In the treatment, the operator can sandwich the biological tissue between the vibration transmission member 23 and the jaw 27. The operator can then feed energy into the sandwiched biological tissue by operating any of the operation buttons 18. When the operator operates the second operation button 18B corresponding to the coagulation and incision mode, the vibration transmission member 23 performs ultrasonic vibration, and imparts heat energy (ultrasonic energy) by frictional motion to the biological tissue. At the same time, high-frequency current flows into the biological tissue between the vibration transmission member 23 and jaw 27 constituting the bipolar electrode, to impart electric energy to the biological tissue. The biological tissue can be coagulated and incised using these two types of energy.

Moreover, when the operator operates the first operation button 18A while the biological tissue is sandwiched between the vibration transmission member 23 and the jaw 27, high-frequency current flows into the biological tissue between the vibration transmission member 23 and jaw 27 constituting the bipolar electrode, to feed electric energy into the biological tissue. The biological tissue can be only coagulated in this way.

If the coagulation and incision treatment or the coagulation treatment is performed on the biological tissue (treatment object) for a long time, the end effector 28 may reach a high temperature exceeding 200° C. as an example. In this embodiment, the first part 44 and second part 45 of the coating 31 are formed on the vibration transmission member 23. The second layer 52 in each of the first part 44 and second part 45 contains the first hollow particles 55 having a heat insulation property. Accordingly, a heat conduction path in the second layer 52 bypasses the first hollow particles 55, as illustrated in FIG. 18. This extends the heat conduction path as compared with the actual film thickness. The heat flux (the amount of heat conducted) in the cut-through direction of the coating 31 can thus be reduced. Therefore, even in the case where the operator unintentionally brings the back surface of the vibration transmission member 23 opposite to the first treatment surface 42 into contact with the surrounding tissue, heat invasion to the surrounding tissue can be prevented.

According to this embodiment, the second layer 52 of the first part 44 and the second layer 52 of the second part 45 of the coating 31 contain the first hollow particles 55, and do not contain the second hollow particles 56. With this structure, too, the heat conduction path in the cut-through direction of the second layer 52 is longer, making it harder for the heat of the end effector 28 to be conducted to the surface of the coating. Therefore, the surrounding tissue is prevented from being damaged by heat even in the case where the end effector 28 is unintentionally brought into contact with the surrounding tissue.

Embodiment 7

Figure 19:
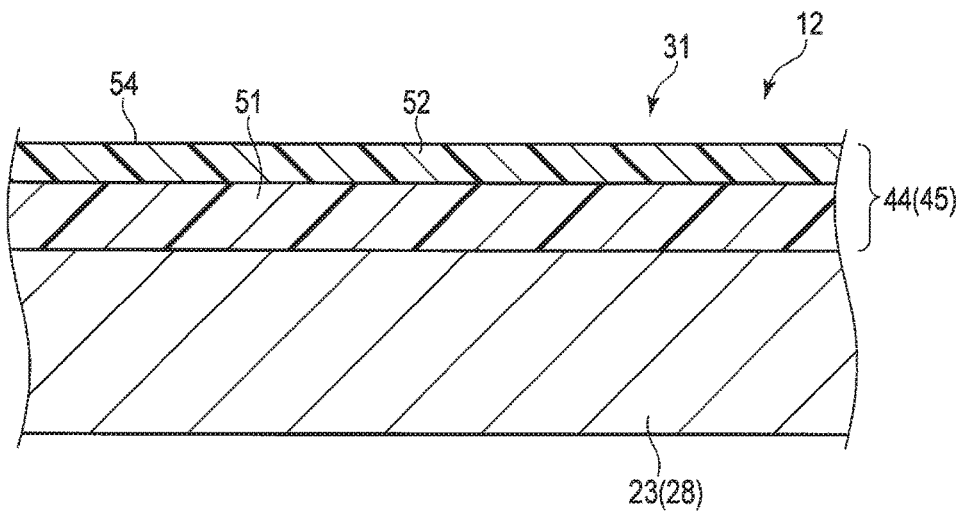
FIG. 19 is a sectional view schematically illustrating each layer of a coating (first part and second part) in a medical device in Embodiment 7.

The following describes a medical device in Embodiment 7, with reference to FIG. 19. The medical device 11 in Embodiment 7 differs from the three-layer structure in Embodiment 1 in that the first part 44 and second part 45 of the coating 31 have a two-layer structure, but is the same as that in Embodiment 1 in the other parts. The following mainly describes the differences from Embodiment 1, and the illustration or description of the same parts as in Embodiment 1 is omitted.

The coating 31 has the first part 44 configured to cover the distal section 23A of the vibration transmission member 23, and the second part 45 configured to cover the intermediate section 23C of the vibration transmission member 23. For example, the coating 31 has an appropriate thickness depending on use in the range of 10 μm to 200 μm.

The first part 44 is provided on the part of the distal section 23A of the vibration transmission member 23 exposed from the sheath 24. In more detail, the first part covers the part of the distal section 23A of the vibration transmission member 23 on the side opposite to the first treatment surface 42 facing the jaw 27. The first part 44 includes: a first layer 51 as a base layer; and a second layer 52 on top of the first layer 51. The outermost second layer 52 is a typical coating made of a resin material such as PEEK. The second layer 52 has projections and depressions 54. The projections and depressions 54 of the second layer 52 can be formed by the same method as the projections and depressions 54 of the first part 44 in Embodiment 1.

The first layer 51 is formed by dispersively mixing first hollow particles 55 and second hollow particles 56 with a base material made of PEEK resin. The first layer has the same structure as the second layer 52 of the coating 31 in Embodiment 1.

The second part 45 is provided on the part of the intermediate section 23C of the vibration transmission member 23 covered with the sheath 24. The second part 45 covers the part of the intermediate section 23C of the vibration transmission member 23 on the distal side of the support section 25 (the node position of ultrasonic vibration). The second part 45 includes: a first layer 51 having the same composition as and formed continuously with the first layer 51 of the first part 44; and a second layer 52 having the same composition as and formed continuously with the second layer 52 of the first part 44. The outermost second layer 52 in the second part 45 is flat.

Typically, if the first hollow particles 55 and the second hollow particles 56 are mixed with the resin as the base material at a predetermined ratio as in the first layer 51 of the coating 31, the film strength of the first layer 51 may decrease. According to this embodiment, since the first layer 51 in which such hollow particles are mixed is not the outermost layer, the film strength can be maintained to reduce the risk of cracking or peeling of the coating 31.

The coating 31 in this embodiment is equally applicable to the coating 31 of the jaw 27, the second coating 71 of the first cover 67, and the second coating 71 of the second cover 68 in Embodiment 3.

Embodiment 8

Figure 20:
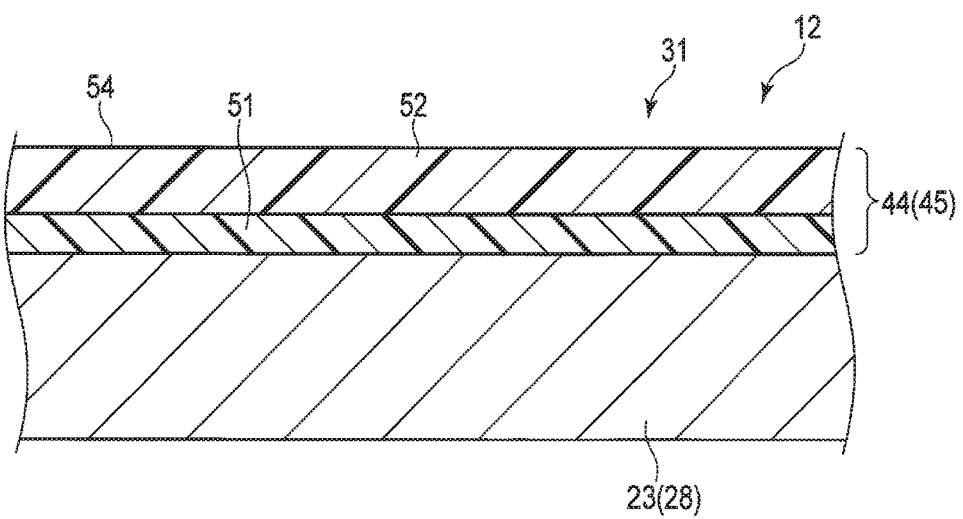
FIG. 20 is a sectional view schematically illustrating each layer of a coating (first part and second part) in a medical device in Embodiment 8.

The following describes a medical device in Embodiment 8, with reference to FIG. 20. The medical device 11 in Embodiment 8 differs from the three-layer structure in Embodiment 1 in that the first part 44 and second part 45 of the coating 31 have a two-layer structure, but is the same as that in Embodiment 1 in the other parts. The following mainly describes the differences from Embodiment 1, and the illustration or description of the same parts as in Embodiment 1 is omitted.

The coating 31 has the first part 44 configured to cover the distal section 23A of the vibration transmission member 23, and the second part 45 configured to cover the intermediate section 23C of the vibration transmission member 23. For example, the coating 31 has an appropriate thickness depending on use in the range of 10 µm to 200 µm.

The first part 44 is provided on the part of the distal section 23A of the vibration transmission member 23 exposed from the sheath 24. In more detail, the first part 44 covers the part of the distal section 23A of the vibration transmission member 23 on the side opposite to the first treatment surface 42 facing the jaw 27. The first part 44 includes: a first layer 51 as a base layer; and a second layer 52 on top of the first layer 51.

The first layer 51 has the same structure as the first layer 51 of the coating 31 in Embodiment 1.

The outermost second layer 52 is formed by dispersively mixing first hollow particles 55 and second hollow particles 56 with a base material made of PEEK resin. The second layer 52 has the same structure as the second layer 52 of the coating 31 in Embodiment 1. The second layer 52 of the first part 44 has projections and depressions 54. The projections and depressions 54 of the second layer 52 can be formed by the same method as the projections and depressions 54 of the first part 44 in Embodiment 1.

The second part 45 is provided on the part of the intermediate section 23C of the vibration transmission member 23 covered with the sheath 24. The second part 45 covers the part of the intermediate section 23C of the vibration transmission member 23 on the distal side of the support section 25 (the node position of ultrasonic vibration). The second part 45 includes: a first layer 51 having the same composition as and formed continuously with the first layer 51 of the first part 44; and a second layer 52 having the same composition as and formed continuously with the second layer 52 of the first part 44. The outermost second layer 52 in the second part 45 is flat.

Typically, if the first hollow particles 55 and the second hollow particles 56 are mixed with the resin as the base material at a predetermined ratio as in the first layer 51 of the coating 31, the adhesion strength (bond strength) to the substrate (the vibration transmission member 23) may decrease. According to this embodiment, since the second layer 52 in which such hollow particles are mixed is not in direct contact with the substrate, the adhesion strength can be maintained to reduce the risk of peeling of the coating.

The coating 31 in this embodiment is equally applicable to the coating of the jaw 27, the second coating 71 of the first cover 67, and the second coating 71 of the second cover 68 in Embodiment 3.

The present invention is not limited to the foregoing embodiments, which may be modified as appropriate without departing from the scope of the present invention. The medical devices 11 of the foregoing embodiments may be combined in any way to form one medical device.

DESCRIPTION OF REFERENCE NUMERALS 11 medical device
23 vibration transmission member
24 sheath
27 jaw
28 end effector
31 coating
36 ultrasonic current supply section
38 high-frequency current supply section
44 first part
45 second part
46 distal component
51 first layer
52 second layer
53 third layer
54 projections and depressions
55 first hollow particle
56 second hollow particle
67 first cover
68 second cover
71 second coating
72 cutter

The invention claimed is:

1. A medical device comprising:
    a probe configured to supply at least one energy to a treatment target; and
    a first coating that coats at least a part of the probe,
    wherein the first coating comprises a resin, and first hollow particles and second hollow particles mixed within the resin,
    wherein each of the first hollow particles is a spherical particle with a hollow interior to provide a hollow space within the resin, and
    wherein each of the second hollow particles is a cylindrical particle having a hole formed therethrough to provide a hollow space within the resin.

2. The medical device according to claim 1,
    wherein the first coating has lower heat conductivity than the probe.

3. The medical device according to claim 1,
    wherein each of the first hollow particles are within a first size distribution, and
    wherein each of the second hollow particles are within a second size distribution different from the first size distribution.

4. The medical device according to claim 1,
    wherein the first coating is arranged as:
    a first layer attached to the probe;
    a second layer overlaid on top of the first layer; and a third layer overlaid on top of the second layer,
wherein the first hollow particles and the second hollow particles are arranged in the second layer and not in the first layer and the third layer.

5. The medical device according to claim 1,
wherein the first coating is arranged as:
a first layer attached to the probe; and
a second layer overlaid on top of the first layer,
wherein the first hollow particles and the second hollow particles are arranged in the first layer and not in the second layer.

6. The medical device according to claim 1, comprising:
a jaw configured to be arranged relative to the probe to clamp the treatment target therebetween,
wherein the probe comprises:
a first side surface facing the jaw; and
a second side surface opposite to the first side surface of the probe,
wherein the first coating coats at least a part of the second side surface of the probe.

7. The medical device according to claim 6,
wherein the probe comprises a distal surface that is distal to the second side surface of the probe, and
wherein the first coating coats the second side surface and not the distal surface.

8. The medical device according to claim 6, further comprising:
a cover configured to at least partially surround the probe in a radial direction of a longitudinal axis of the probe, wherein the cover has a first side facing the probe and a second side opposite to the first side of the cover; and
a second coating that coats at least a part of the second side of the cover, wherein the second coating has lower heat conductivity than the probe.

9. The medical device according to claim 1, comprising a tubular member,
wherein the at least one energy supplied by the probe is vibration,
wherein a first portion of the probe is arranged inside the tubular member, and a second portion of the probe is arranged outside the tubular member, and
wherein the first coating coats at least a portion of the second portion of the probe.

10. The medical device according to claim 1,
wherein the probe comprises:
a cutter face configured to incise the treatment target; and
a surface opposite to the cutter face, and
wherein the first coating coats at least a part of the surface opposite to the cutter face.

11. The medical device according to claim 1, comprising:
a jaw configured to be arranged relative to the probe to clamp the treatment target therebetween,
wherein the jaw comprises:
a first side surface facing the probe; and
a second side surface opposite to the first side surface of the jaw; and
a second coating that coats at least a part of the second side surface of the jaw,
wherein the second coating comprises the resin, and the first hollow particles and the second hollow particles mixed within the resin.

12. The medical device according to claim 1,
wherein the probe is heated in the process of supplying the at least one energy to the treatment target, and
wherein the first coating defines a plurality of projections and depressions.

13. The medical device according to claim 12,
wherein the probe extends along a longitudinal axis from a distal end of the probe to a proximal end of the probe, and
wherein the first coating is arranged as:
a first layer attached to the probe; and
a second layer overlaid on top of the first layer, wherein the second layer comprises:
a first part having the projections and depressions; and
a flat second part proximal to the first part along the longitudinal axis.

14. The medical device according to claim 1,
wherein the probe is configured to be connected to one or more of:
an ultrasonic energy supply to receive ultrasonic energy; and
a high-frequency energy supply to receive high-frequency energy,
as the at least one energy supplied by the probe to the treatment target.

15. The medical device according to claim 1,
wherein the at least one energy is any of ultrasonic vibration energy, high-frequency energy, heat energy, light energy, an electromagnetic wave, and kinetic energy.

16. The medical device according to claim 1,
wherein the at least one energy comprises ultrasonic vibration,
wherein the probe has an untreated surface that is not treated, and
wherein the first coating coats at least a part of the untreated surface.

17. The medical device according to claim 1,
wherein the second hollow particles have a particle size that is $1/100$ or less of a particle size of the first hollow particles.

18. The medical device according to claim 1,
wherein the first coating has a textured surface.

19. The medical device according to claim 18,
wherein the textured surface of the first coating has a uniform pitch.

20. The medical device according to claim 1, comprising a jaw,
wherein the probe comprises:
a first face that opposes the jaw; and
a second face that is opposite to the first face,
wherein the first coating coats at least a part of the second face of the probe.

21. The medical device according to claim 1, comprising:
a sheath; and
a second coating,
wherein the at least one energy is ultrasonic vibration transmitted by the probe,
wherein the probe comprises a distal portion, an intermediate portion and a proximal portion arranged along a longitudinal axis of the probe,
wherein the first coating coats at least a part of the distal portion of the probe,
wherein the intermediate portion is surrounded by the sheath, and is connected to the proximal portion at a node position of the ultrasonic vibration,
wherein the second coating coats an entire circumference of at least a part of the intermediate portion, and
wherein the second coating comprises the resin, and the first hollow particles and the second hollow particles mixes within the resin.

22. The medical device according to claim 1, wherein the at least one energy comprises high-frequency energy.

23. The medical device according to claim 1, wherein the first coating is arranged as a first layer including the first hollow particles and the second hollow particles, and a second layer not including the first hollow particles and the second hollow particles.

* * * * *

UNITED STATES PATENT AND TRADEMARK OFFICE
CERTIFICATE OF CORRECTION

PATENT NO. : 10,357,273 B2
APPLICATION NO. : 15/261145
DATED : July 23, 2019
INVENTOR(S) : Tsunetaka Akagane It is certified that error appears in the above-identified patent and that said Letters Patent is hereby corrected as shown below:

On the Title Page

(30) Foreign Application Priority Data should read:
May 29, 2015  (JP)   2015-110243

Signed and Sealed this
Tenth Day of December, 2019

Andrei Iancu
*Director of the United States Patent and Trademark Office*